US010786656B2

(12) United States Patent
Ogata et al.

(10) Patent No.: US 10,786,656 B2
(45) Date of Patent: Sep. 29, 2020

(54) METHODS AND DEVICES FOR RECANALIZATION OF OCCLUDED BODY VESSELS USING A DOUBLE-SIDED GUIDEWIRE

(75) Inventors: Wayne Ogata, San Ramon, CA (US); Osamu Katoh, Nagoya (JP)

(73) Assignee: ASAHI MEDICAL TECHNOLOGIES, INC., Pleasanton, CA (US)

( * ) Notice: Subject to any disclaimer, the term of this patent is extended or adjusted under 35 U.S.C. 154(b) by 323 days.

(21) Appl. No.: 13/574,587

(22) PCT Filed: Feb. 14, 2011

(86) PCT No.: PCT/US2011/024809
§ 371 (c)(1),
(2), (4) Date: Jul. 20, 2012

(87) PCT Pub. No.: WO2011/094767
PCT Pub. Date: Aug. 4, 2011

(65) Prior Publication Data
US 2012/0289983 A1 Nov. 15, 2012

Related U.S. Application Data

(60) Provisional application No. 61/298,549, filed on Jan. 26, 2010.

(51) Int. Cl.
*A61B 17/22* (2006.01)
*A61M 25/09* (2006.01)
*A61M 25/01* (2006.01)

(52) U.S. Cl.
CPC ......... *A61M 25/0905* (2013.01); *A61B 17/22* (2013.01); *A61B 2017/22044* (2013.01); *A61B 2017/22094* (2013.01); *A61M 25/01* (2013.01)

(58) Field of Classification Search
CPC ............ A61M 25/09; A61M 25/09016; A61M 25/09025; A61M 25/09033;
(Continued)

(56) References Cited

U.S. PATENT DOCUMENTS 5,546,958 A * 8/1996 Thorud ............ A61M 25/0905 600/434
5,776,079 A 7/1998 Cope et al.
(Continued)

OTHER PUBLICATIONS http://www.thefreedictionary.com/progressive.*
(Continued)

*Primary Examiner* — Elizabeth Houston
*Assistant Examiner* — Socrates L Boutsikaris
(74) *Attorney, Agent, or Firm* — Troutman Pepper Hamilton Sanders LLP (Rochester)

(57) ABSTRACT

Devices and methods for recanalization of occluded body vessels using novel guidewires. A novel double-sided guidewire comprises a cross-section tapering from a more rigid middle section towards more flexible head sections. A first head of the guidewire is inserted into the occluded body vessel in a retrograde direction to traverse an occlusion. The guidewire is further advanced in the retrograde direction such that the first head and a portion of the middle section are retrieved from the body, thereby positioning the remainder of the guidewire traversing the occlusion in an antegrade direction and allowing for over the wire recanalization techniques in the antegrade direction.

6 Claims, 12 Drawing Sheets

(58) Field of Classification Search

CPC ........ A61M 25/09041; A61M 25/0905; A61M 2025/09058; A61M 2025/09075; A61M 2025/09175; A61M 2025/0915; A61M 2025/09108; A61B 2017/22044; A61B 2017/22094; A61B 5/6851

USPC .......... 606/159, 222–223, 144–148; 600/585

See application file for complete search history.

(56) References Cited

U.S. PATENT DOCUMENTS

| | | | | |
|---|---|---|---|---|
| 7,621,880 | B2 * | 11/2009 | Ryan | A61M 25/09 600/585 |
| 2006/0155363 | A1 * | 7/2006 | LaDuca | A61F 2/844 623/1.16 |
| 2007/0016106 | A1 | 1/2007 | Ramaiah et al. | |
| 2007/0083220 | A1 * | 4/2007 | Shamay | A61B 17/3207 606/159 |
| 2008/0171952 | A1 * | 7/2008 | Mishima | 600/585 |
| 2008/0200839 | A1 * | 8/2008 | Bunch | A61M 25/09 600/585 |
| 2008/0306499 | A1 | 12/2008 | Katoh et al. | |
| 2010/0256616 | A1 | 10/2010 | Katoh et al. | |

OTHER PUBLICATIONS

International Search Report for International Patent Application No. PCT/US2011/024809 (Nov. 15, 2011).

Office Action for Japanese Patent Application No. 2012-550222, dated Nov. 4, 2015.

Office Action for Japanese Patent Application No. 2012-550222, dated Nov. 11, 2014.

Office Action for Japanese Patent Application No. 2012-550222, dated Nov. 29,2016, pp. 1-5.

* cited by examiner

METHODS AND DEVICES FOR RECANALIZATION OF OCCLUDED BODY VESSELS USING A DOUBLE-SIDED GUIDEWIRE

FIELD OF THE INVENTION

The present embodiments relate generally to methods and devices for recanalizing occluded body vessels, and in particular to using a novel double-sided guidewire to penetrate an occlusion in a retrograde direction to allow for recanalization in an antegrade direction.

DESCRIPTION OF THE RELATED ART

Chronic total occlusion (CTO) is the complete blockage of a vessel and usually has serious consequences if not treated in a timely fashion. The blockage could be due to atheromatous plaque or old thrombus.

One of the common procedures for treating CTOs of the coronary arteries is percutaneous trans-luminal coronary angioplasty (PTCA). During a PTCA procedure, a small incision is, typically, made in the groin. A guiding catheter is introduced over a guidewire into the femoral artery and advanced to the occlusion. Frequently, with gentle maneuvering, the guidewire is able to cross the stenosis. Then, a balloon-tipped angioplasty catheter is advanced over the guidewire to the stenosis. The balloon is inflated, separating or fracturing the atheroma. Commonly, a stent is subsequently placed. Some of the common steps involved in the PTCA procedure are the simultaneous injection of a contrast agent in the contra-lateral vessel, getting backup force or stabilization for a guidewire (which could invoke additional personnel to handle the catheter), puncturing the plaque, drilling or rotating the guidewire to push it through the dense plaque, etc. Because of the stiff resistance sometimes offered by dense plaque, one could be forced to use rigid wires. Occasionally, the wires could puncture the vessel wall calling for remedial measures.

Percutaneous treatment of coronary chronic total occlusions remains one of the major challenges in interventional cardiology. Recent data have shown that successful percutaneous recanalization of chronic coronary occlusions results in improved survival, as well as enhanced left ventricular function, reduction in angina, and improved exercise tolerance.

However, because of the perceived procedural complexity of angioplasty in CTOs, it still represents the most common reason for referral to bypass surgery, or for choosing medical treatment.

The most common percutaneous coronary intervention (PCI) failure mode for CTOs is the inability to successfully pass a guidewire across the lesion into the distal true lumen of the vessel. To date, there is no consensus on how best to treat CTOs after attempts with conventional guidewires have failed. Different strategies and specific devices for CTOs have been developed, including the subintimal tracking and reentry with side branch technique, parallel wire technique, IVUS guided technique, and retrograde approach. However, none of these alternate strategies have provided satisfactory results for the most challenging of the CTOs.

Therefore, it would be desirable to have alternate techniques and devices for simplifying the recanalization of CTOs while overcoming some of the shortcomings of current techniques. CTOs that are difficult and time consuming to recanalize would benefit from novel CTO recanalization approaches.

SUMMARY OF THE INVENTION

Disclosed are embodiments of devices and methods for recanalizing an occluded body vessel by using a novel double-sided guidewire.

In one embodiment, a device for recanalizing an occluded vessel comprises a first guidewire having a head and a tail; and a second guidewire having a head and a tail; wherein the tail of the first guidewire is configured to be coupled to the tail of the second guidewire; and wherein the first guidewire is configured to be advanced into the occluded vessel in a retrograde direction, and the head of the second guidewire is configured to be positioned in the occluded vessel in an antegrade direction.

In one aspect, a cross-sectional area of the guidewires increases from the head towards the tail.

In one aspect, the first or second guidewire comprises a core wire. The core wire may comprise a substantially flat cross-section. In one aspect, the device comprises a layer of structural polymer over the core wire. In one aspect, an outer surface of the first or second guidewire is coated with a hydrophilic coating for ease of navigation through tortuous passageways.

In one aspect, the device is separable into the first and second guidewires.

In one aspect, the first guidewire or the second guidewire is extendable.

In one aspect, the first guidewire and the second guidewire each have a fixed length.

In one embodiment, a method for positioning a guidewire in an occluded body vessel comprises advancing a first guidewire in the occluded body vessel in a retrograde direction, wherein the first guidewire comprises a head and a tail, and wherein the tail of the first guidewire is configured to be coupled to a tail of a second guidewire; penetrating an occlusion using the head of the first guidewire; advancing the first guidewire through the occlusion such that the first guidewire traverses the occlusion; coupling the tail of the first guidewire to the tail of the second guidewire; and advancing the coupled first and second guidewires through the occluded body vessel in the retrograde direction until the first guidewire and the tail of the second guidewire are retrieved out of the occluded body vessel; thereby positioning the second guidewire such that it traverses the occlusion in an antegrade direction. The second guidewire comprises a head. The method may comprise extending the first and/or the second guidewire. The method may further comprise de-coupling the first guidewire from the second guidewire after the first guidewire and the tail of the second guidewire are retrieved out of the occluded body vessel.

In another embodiment, a method for positioning a guidewire in an occluded body vessel comprises advancing a guidewire in the occluded body vessel in a retrograde direction, wherein the guidewire comprises a first head, a middle section, and a second head, wherein a cross-sectional area of the guidewire decreases from the middle section towards the first and second heads; traversing an occlusion using the first head of the guidewire; and advancing the guidewire through the occluded body vessel in the retrograde direction until the first head and a portion of the middle section are retrieved out of the occluded body vessel; thereby positioning the guidewire such that it traverses the occlusion in an antegrade direction.

Other embodiments and variations are presented in the detailed description, as follows.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION

Although the detailed description contains many specifics, these should not be construed as limiting the scope of the invention but merely as illustrating different examples and aspects of the invention. It should be appreciated that the scope of the invention includes other embodiments not discussed in detail herein. Various other modifications, changes and variations which will be apparent to those skilled in the art may be made in the arrangement, operation and details of the methods and devices of the present invention disclosed herein without departing from the spirit and scope of the invention as described here.

Figure 1:
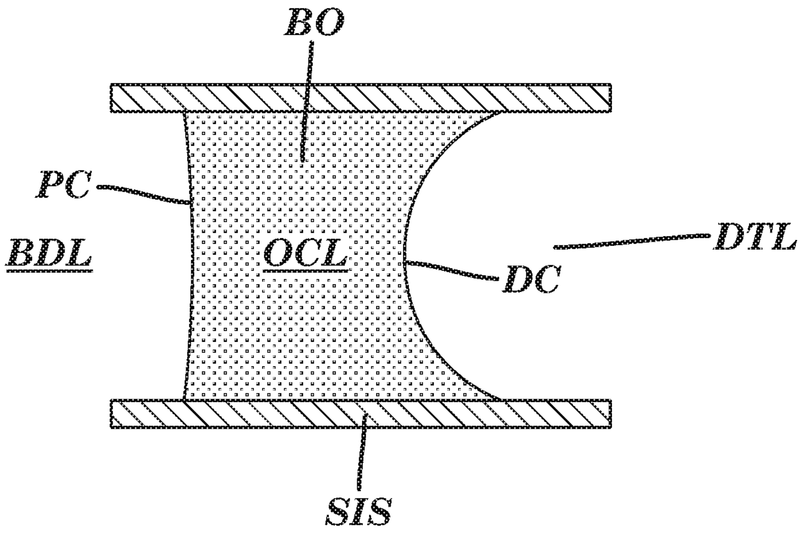
FIG. 1 shows an occluded body vessel.

A schematic diagram of a portion of an occluded body vessel BDL is shown in FIG. 1. The body vessel BDL could be any vessel or artery in which blood flows through the hollow tubular cavity. An occlusion OCL within the body vessel BDL may obstruct the blood flow and could have fatal consequences. Typically, treatment procedures may involve approaching the occlusion from an antegrade and/or a retrograde direction. The occlusion OCL comprises a distal cap DC, a proximal cap PC, and an occlusion body BO therebetween. In the combined, antegrade-retrograde approach, the distal cap DC is typically approached from a retrograde direction, whereas the proximal cap PC is typically approached from an antegrade direction. The occlusion OCL could be atheromatous plaque, old thrombus, or similar other deposit. One method of recanalizing the occlusion OCL is by using guidewire techniques, wherein a guidewire penetrates the occlusion OCL and a catheter recanalizes the vessel.

Depending on the type and the composition of the occlusion OCL, it may be difficult to successfully penetrate the occlusion OCL using standard guidewire techniques. In particular, the distal cap DC of the occlusion may be composed of dense, fibrous tissue with fibrocalcific regions. Generally, it may be necessary to use a guidewire of sufficient rigidity to successfully penetrate the distal cap DC. Also, it may generally be necessary to apply substantial force in order to penetrate the distal cap DC of the occlusion and recanalize the body vessel.

When traversing the occlusion in an antegrade direction, it has been a challenge to successfully penetrate and traverse the distal cap DC and enter the distal true lumen DTL without entering into subintimal space SIS. This is so because, combined with its fibrous composition, the distal cap DC of the occlusion often assumes a morphology that renders penetration difficult, as the guidewire is likely to be deflected away from the fibrous interior surface of the distal cap DC (see FIG. 1). The difficulties in penetrating the distal cap DC of the occlusion often lead to the guidewire slipping away from the interior surface of the distal cap DC and entering into subintimal space SIS. The penetration of the subintimal space SIS may lead to the puncturing of the wall of the body vessel, which may cause bleeding as well as other undesirable side effects. Furthermore, by penetrating the subintimal space SIS instead of the distal cap DC, it is substantially more difficult for a catheter to advance into the distal true lumen DTL to complete the recanalization.

Embodiments of the present invention relate generally to devices, systems, and methods for simplifying the process of recanalization of an occluded body vessel. Specifically, one aspect of the present embodiments discloses devices and methods for positioning a guidewire within an occluded body vessel for recanalization without the need for an exchange. In one embodiment, a first guidewire may be coupled to a second guidewire is inserted into the occluded body vessel in a retrograde direction. The first guidewire may then penetrate the distal cap DC from the retrograde direction and advances through the occlusion. Thereafter, the first guidewire may be retrieved from the body vessel along with a portion of the second guidewire, leaving the second guidewire positioned within the occlusion in the antegrade direction. With the second guidewire positioned in the occlusion in an antegrade direction, over-the-wire recanalization techniques that are well known in the art may be performed to recanalize the body vessel. Furthermore, it is contemplated that the embodiments described herein may be applied analogously in the antegrade approach, wherein a first guidewire coupled to a second guidewire may be inserted into the occluded body vessel in an antegrade direction, and upon completion of the procedure, the second guidewire may be positioned within the occlusion in the retrograde direction.

Figure 2A:
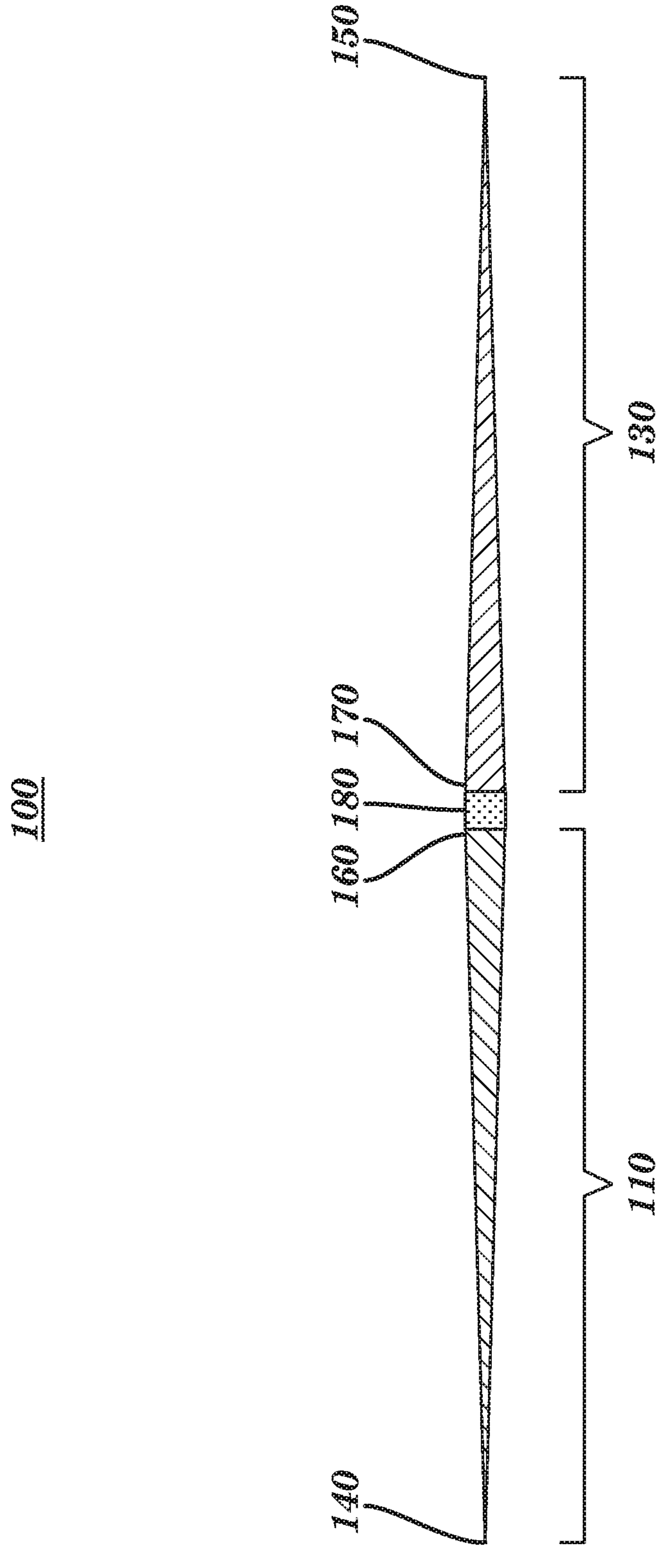
FIG. 2A shows an embodiment of a double-sided guidewire device comprising a first guidewire coupled to a second guidewire tail-to-tail.

One embodiment of the double-sided guidewire device is shown in FIG. 2A. The device 100 comprises a first guidewire 110 and a second guidewire 130. The first guidewire 110 comprises a head 140 and a tail 160. The second guidewire 130 comprises a head 150 and a tail 170. The tail 160 of the first guidewire 110 is configured to be coupled with the tail 170 of the second guidewire 130 by a coupling means 180.

In one embodiment, the coupling means 180 is configured to securely lock the first guidewire 110 and the second guidewire 130 to prevent separation during the guidewire placement procedure. Additionally and optionally, the coupling means 180 may be configured to provide quick and easy detachment of the two guidewires. In one embodiment, the coupling means 180 may comprise a male portion (not shown) disposed on the tail of either the first or the second guidewire, and a female portion (not shown) disposed on the tail of the other guidewire, wherein the male portion is configured to be inserted into the female portion. In one embodiment the male portion may be spring loaded to more securely attach inside the female portion. Alternatively, coupling may be achieved by other means of coupling, connecting, or extending guidewires such as the use of magnets or a screwing mechanism.

Additionally, as seen in FIG. 2A, a cross-sectional area of the first guidewire 110 is configured to progressively increase from the head 140 towards the tail 160. Similarly, a cross-sectional area of the second guidewire 130 is configured to progressively increase from the head 150 towards the tail 170, such that the first and the second guidewires assume substantially tapered configurations. The tapered configuration may be advantageous in that the narrow head may be configured to effectively traverse through the vascular matrix and to penetrate the occlusion, whereas the larger tail is configured to allow a physician to manipulate the guidewire during the operation. Alternatively and optionally, a cross-sectional area of the first guidewire 110 and/or the second guidewire 130 may be configured to be substantially unchanged throughout the lengths of the guidewires.

It is noted that the flexibility of the first and the second guidewires may vary over their respective lengths. In one embodiment, the heads of the guidewires are substantially flexible, and the flexibility progressively decreases towards the tails.

Figure 2B:
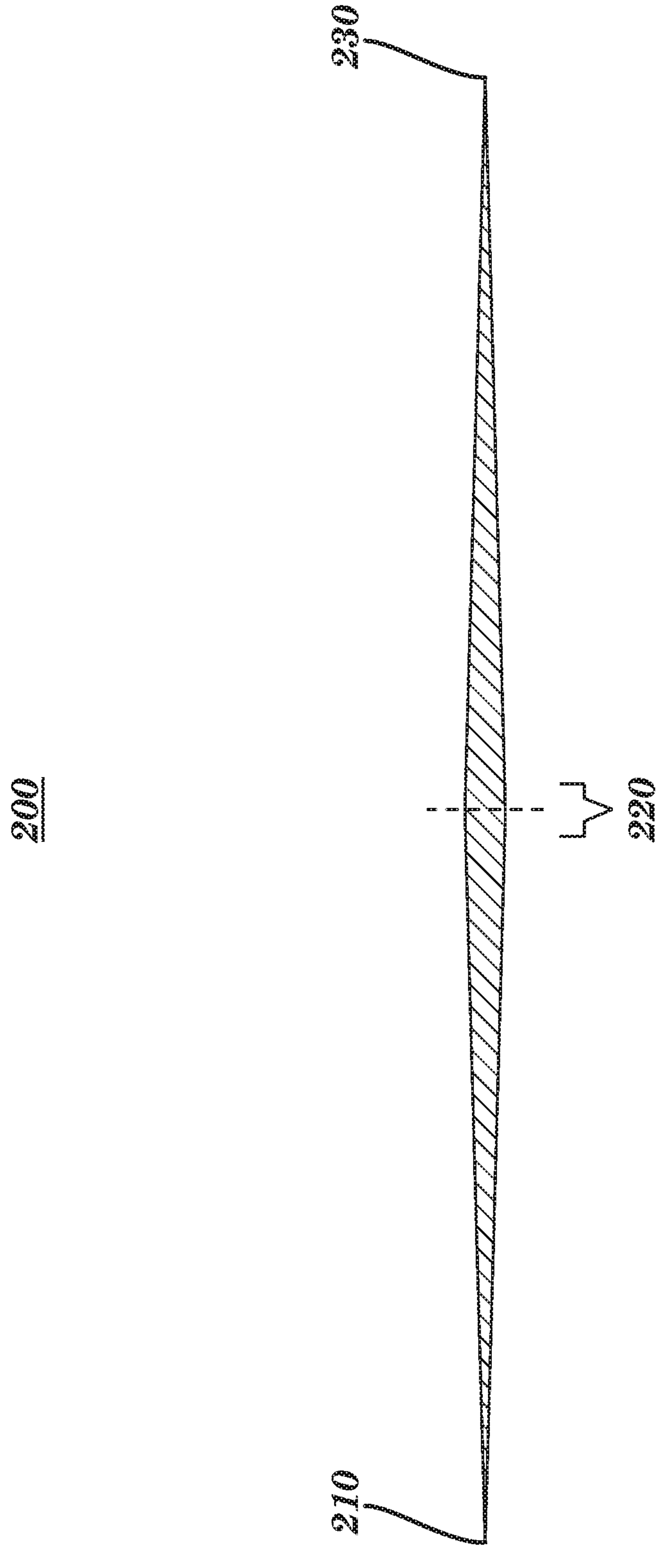
FIG. 2B shows another embodiment of a double-sided guidewire device comprising a middle section that tapers towards two head sections.

Another embodiment of the present invention is shown in FIG. 2B. FIG. 2B shows a single guidewire embodiment, wherein a guidewire device 200 comprises a first head 210, a middle section 220, and a second head 230. The cross-sectional area of the guidewire 200 may be minimal at the heads 210 and 230, and may increase towards the middle section 220, providing a tapered configuration similar to the embodiment shown in FIG. 2A.

Figure 3:
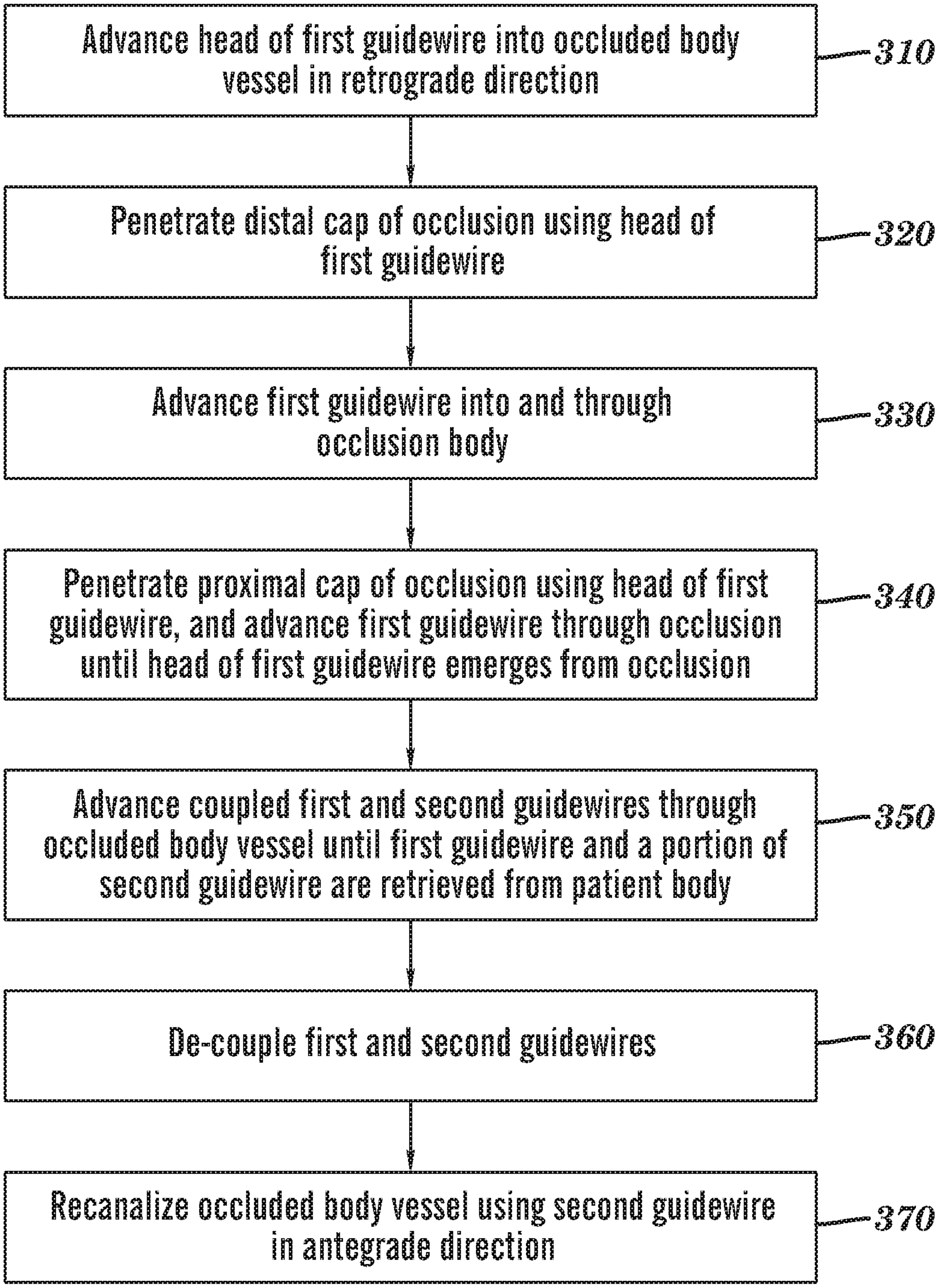
FIG. 3 is a flow diagram illustrating a method for recanalizing an occluded body vessel using a double-sided guidewire device.
Figure 4A:
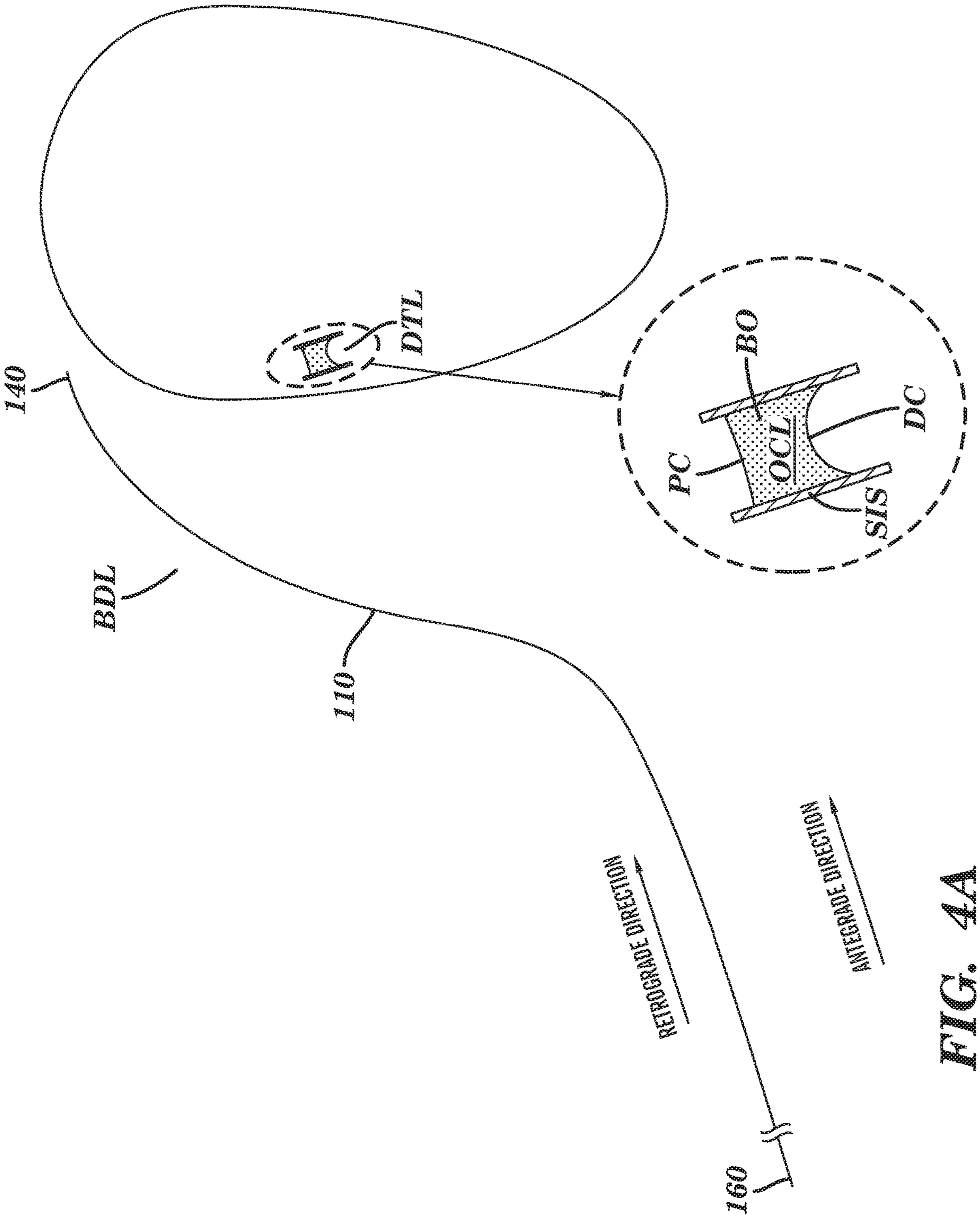
FIGS. 4A-4H depict various stages of the recanalization procedure of FIG. 3, according to an embodiment using a double-sided guidewire with a first and second guidewire coupled tail-to-tail.

FIG. 3 is a flow diagram illustrating the positioning of a guidewire device in an occluded body vessel, in accordance with one embodiment of the present invention and with reference to FIGS. 4A-4G. At step 310, the head 140 of the first guidewire 110 is advanced through the occluded body vessel BDL in a retrograde direction (FIG. 4A). Retrograde insertion may involve navigating the guidewire through narrow septal channels of the coronary vasculature, depending on the position of the occlusion.

Figure 4B:
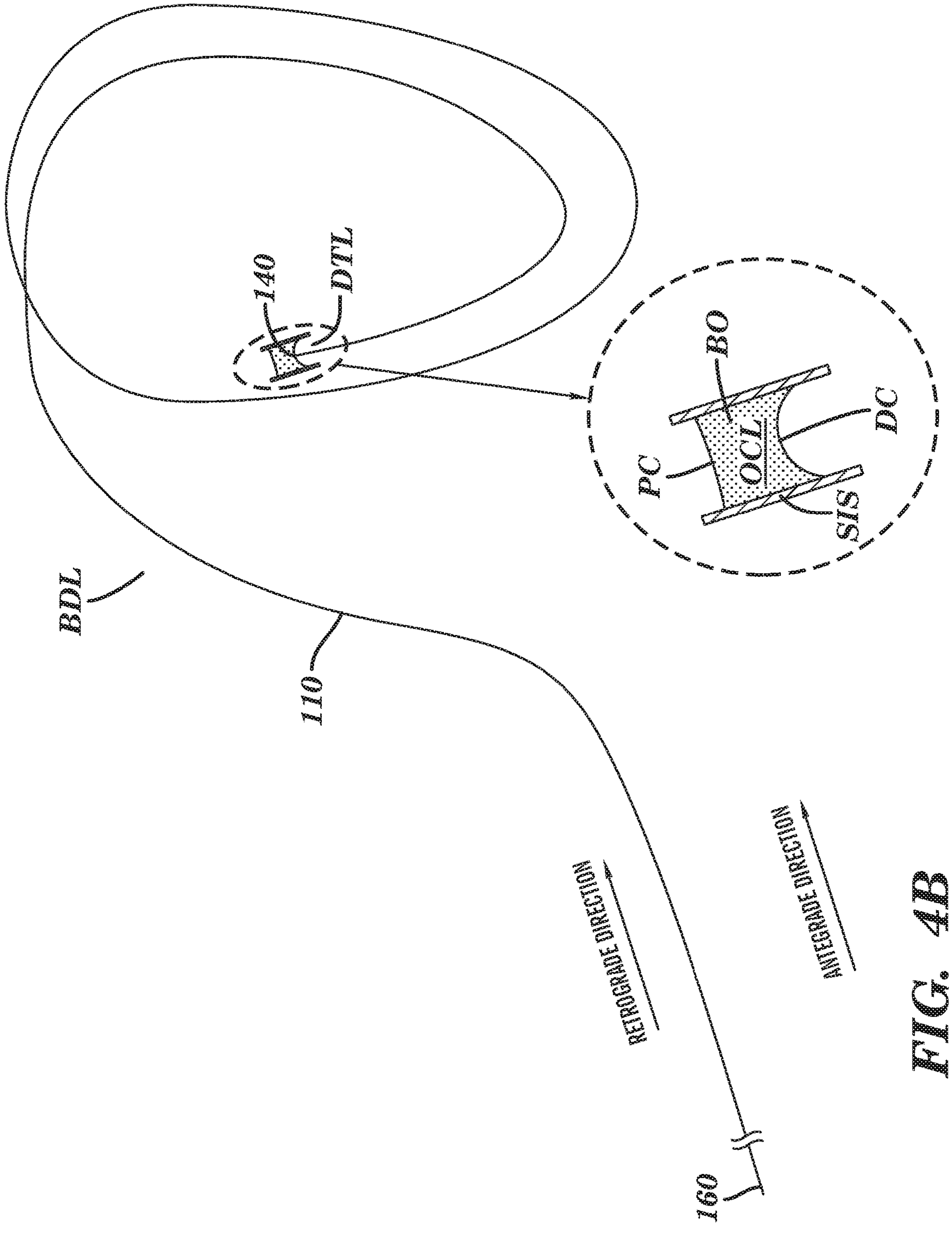
Figure 4C:
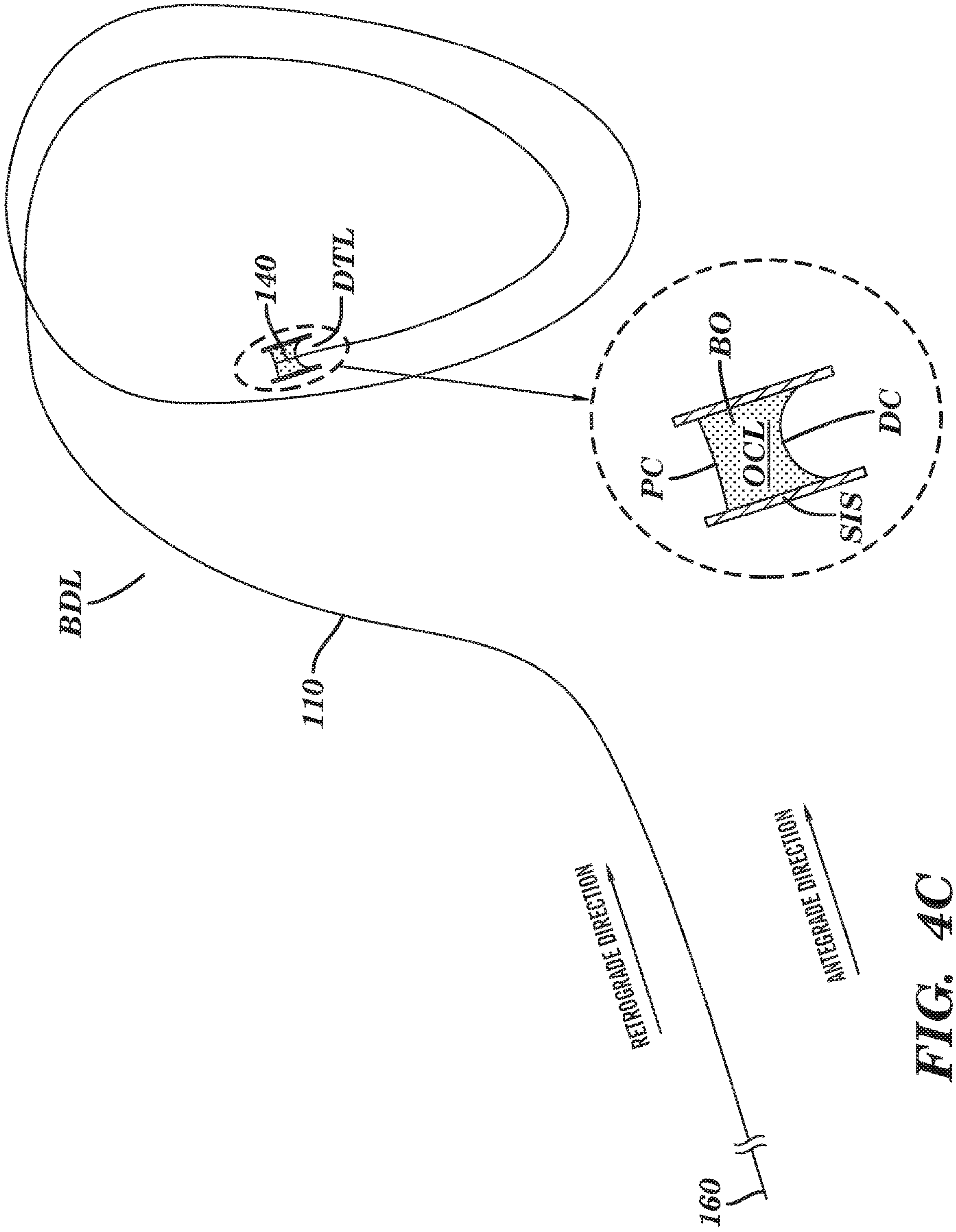
Figure 4D:
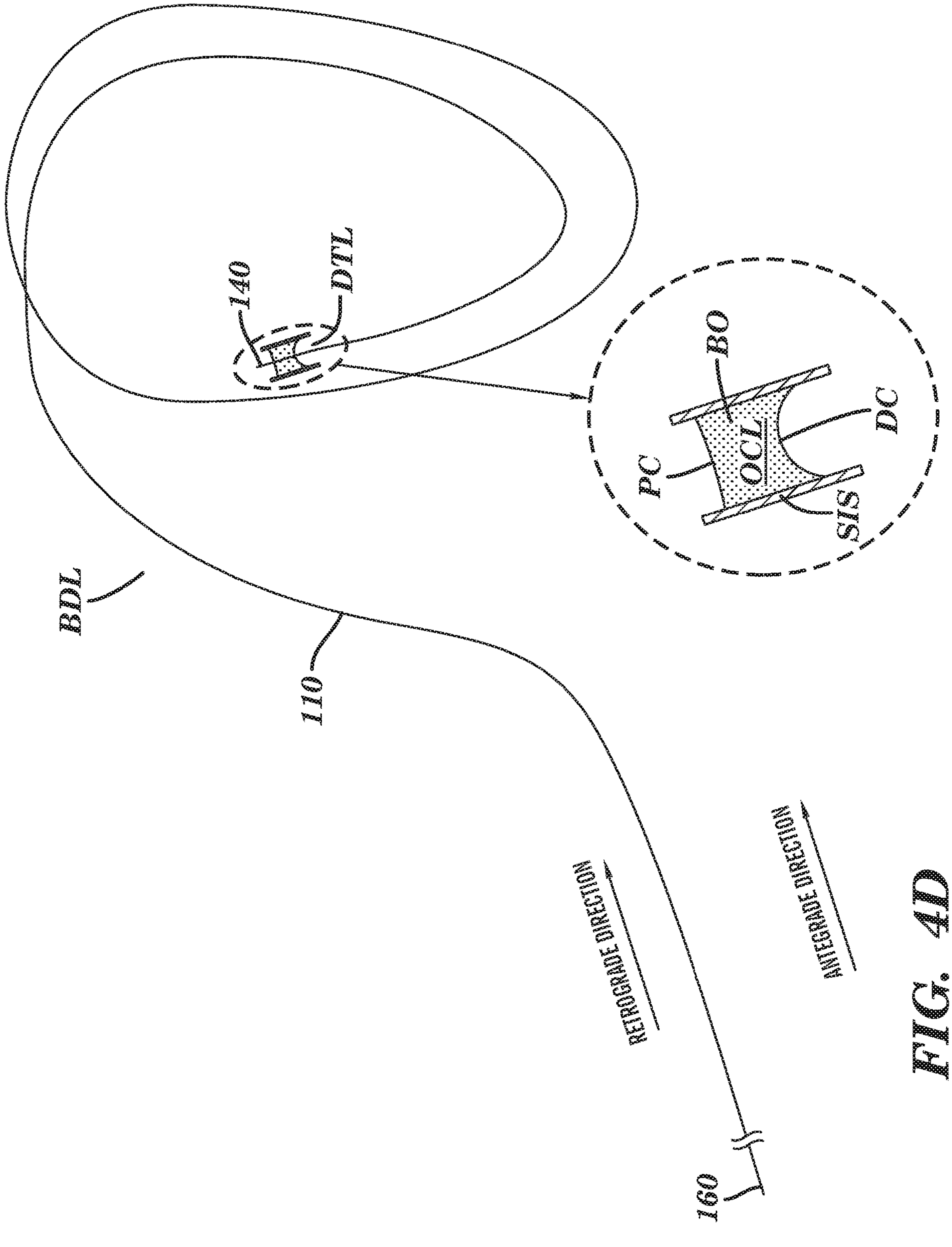

At step 320, the head 140 of the first guidewire 110 penetrates the distal cap DC of the occlusion (FIG. 4B). At step 330, the first guidewire 110 is advanced into and through the body BO of the occlusion (FIG. 4C). At step 340, the head 140 of the first guidewire 110 penetrates the proximal cap PC of the occlusion, and the first guidewire 110 is further advanced through the occlusion body BO until the head 140 emerges from the occlusion OCL (FIG. 4D). At this point, the head 140 of the first guidewire 110 may have substantially fully traversed the occlusion OCL in a retrograde direction.

Figure 4E:
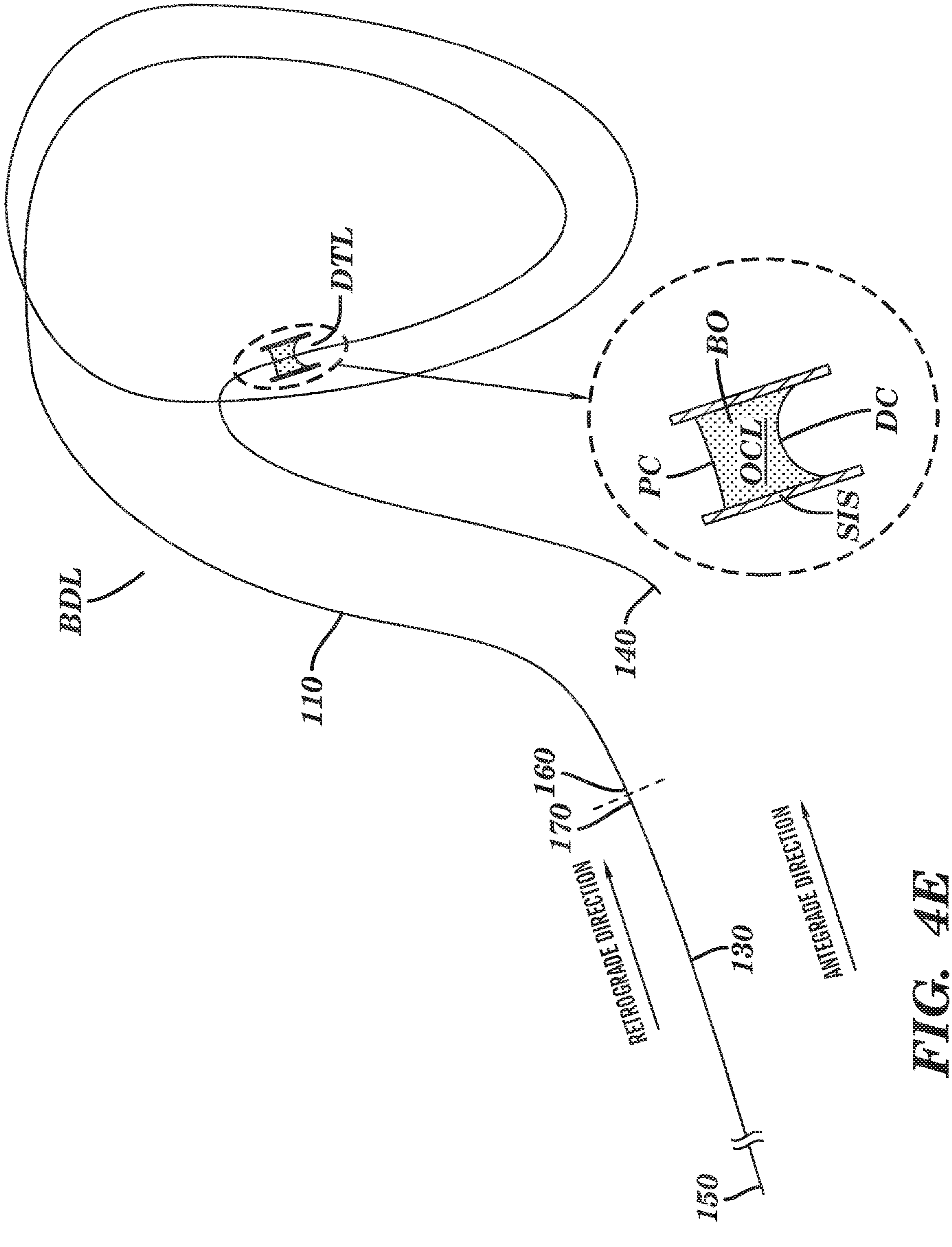
Figure 4F:
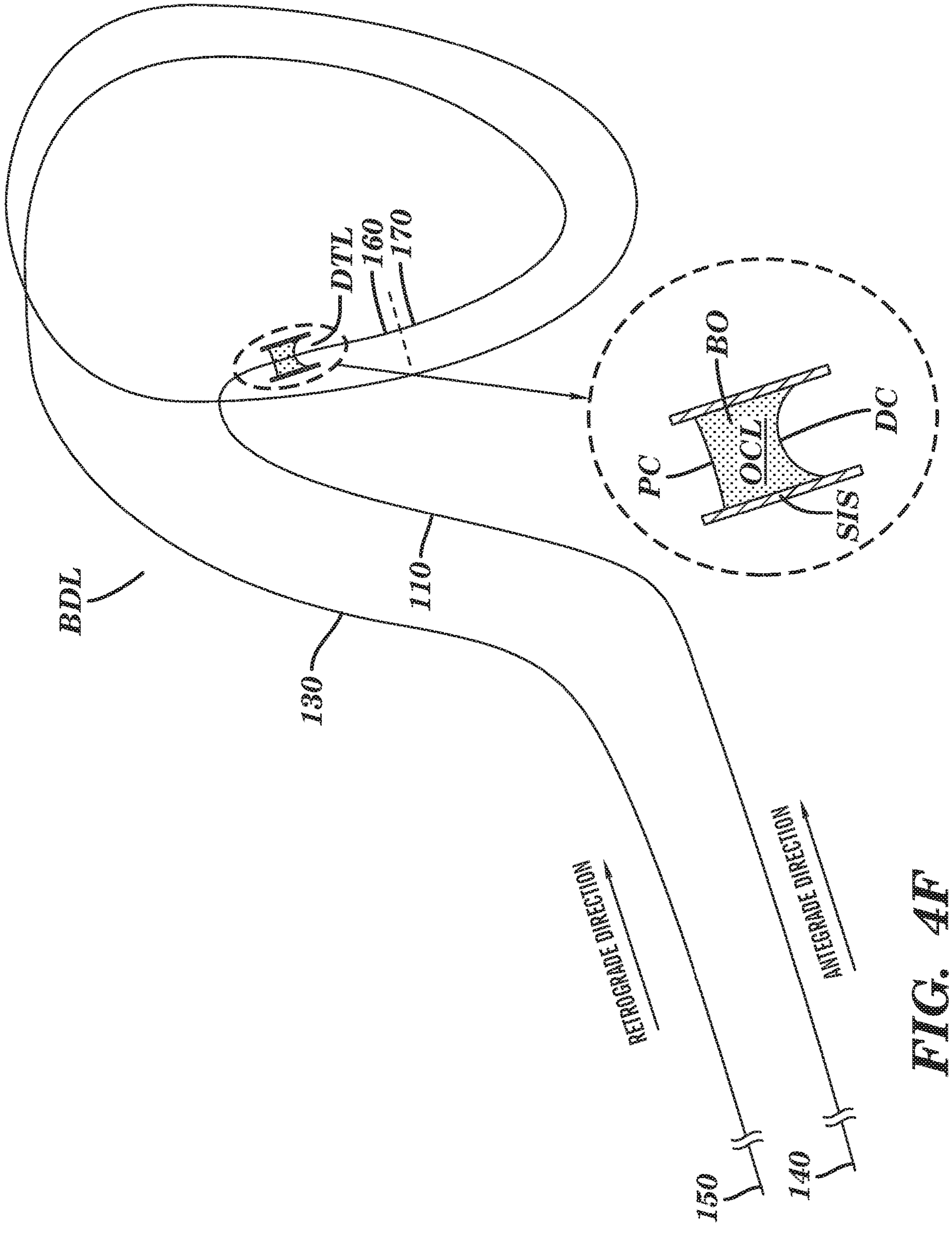
Figure 4G:
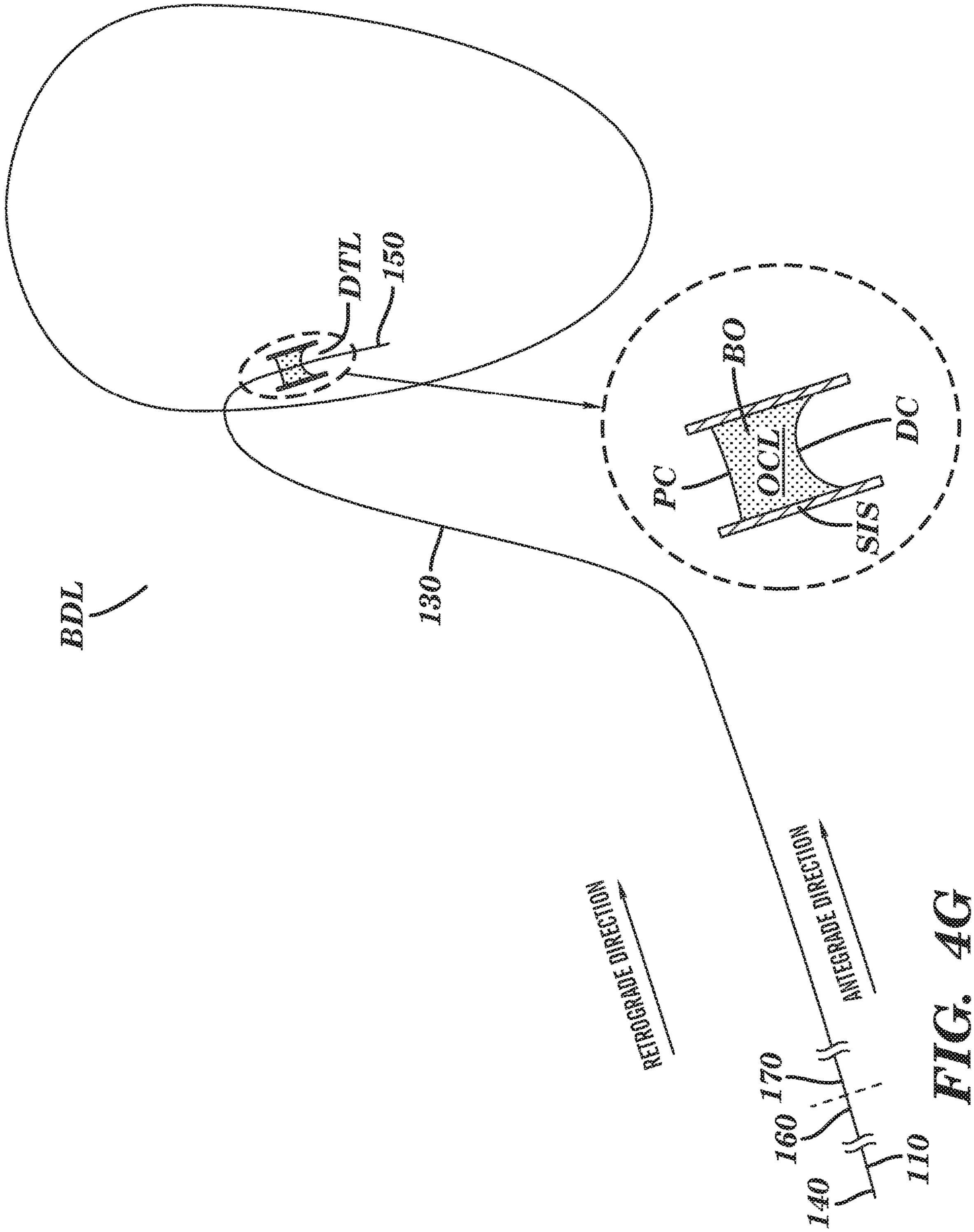

At step 350, the first guidewire 110, coupled with the second guidewire 130, are advanced through the occluded body vessel BDL (FIG. 4E). For this step, when the second guidewire 130 is not already coupled with the first guidewire 110, the physician couples the two guidewires (as described above) prior to performing step 350. Retrograde advancement of the two coupled guidewires then proceeds until the first guidewire 110, and a portion of the second guidewire 130, are retrieved from the body of the patient (FIG. 4F-4G).

Figure 4H:
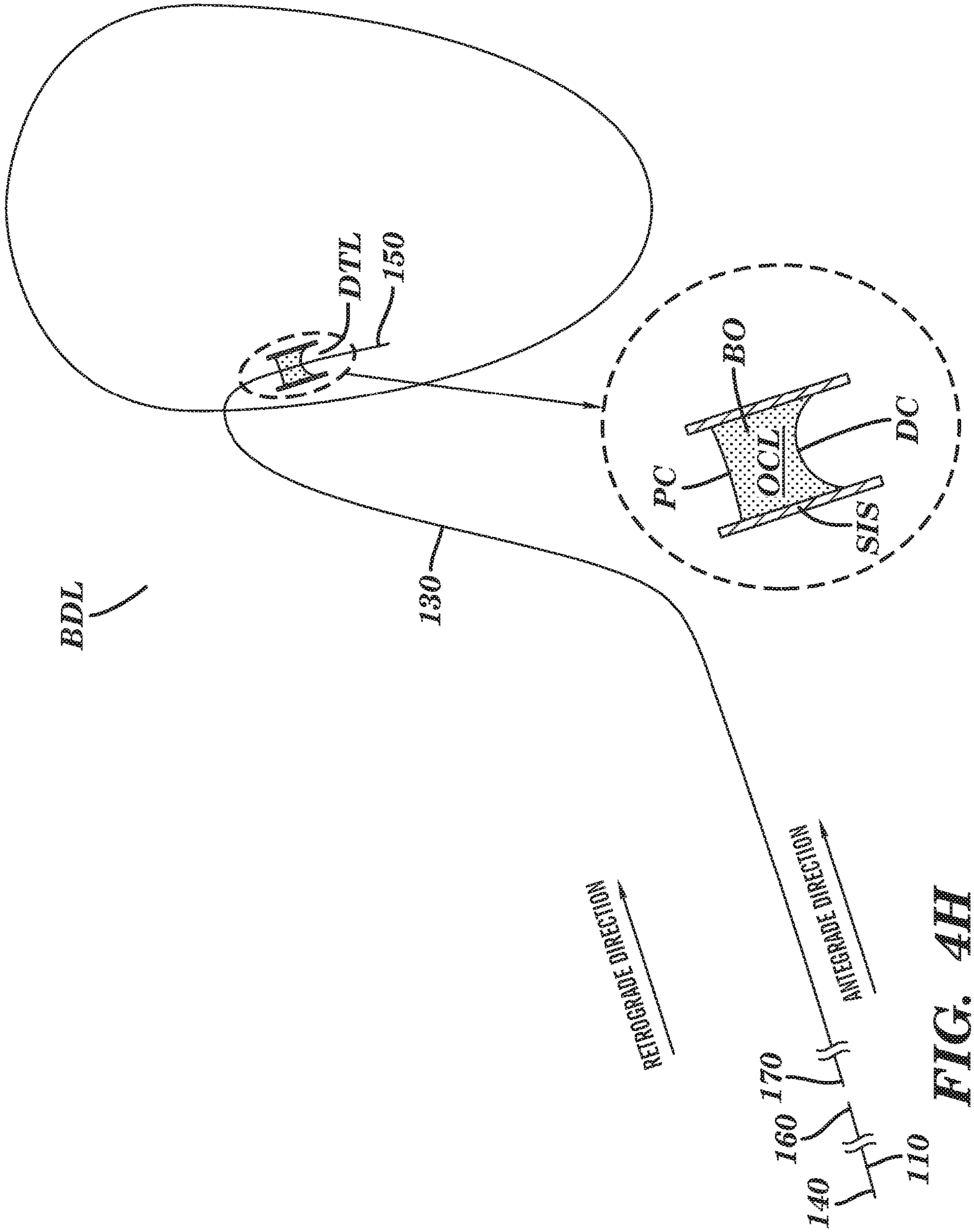

At this point, the entire first guidewire 110, and the tail 170 of the second guidewire 130, are positioned outside of the patient's body, while the head 150 of the second guidewire 130 is positioned within the distal true lumen DTL of the occluded body vessel BDL, with a portion of the second guidewire 130 traversing the occlusion OCL in an antegrade direction. At step 360, the tail 160 of the first guidewire and the tail 170 of the second guidewire may be de-coupled (FIG. 4H) by disengaging the coupling means. At step 370, with the tail 170 of the second guidewire positioned outside the patient and a portion of the second guidewire 130 traversing the occlusion, over the wire recanalization techniques that are well known in the art can be performed in an antegrade direction to recanalize the occluded body vessel BDL. In particular, the controlled antegrade and retrograde tracking (CART) techniques disclosed in the co-pending U.S. patent application Ser. No. 12/150,111, and the recanalization techniques combining the antegrade and retrograde approach with the use of radiofrequency energy as disclosed in PCT International Application Ser. No. PCT/US2008/077403, both by the same inventors and incorporated herein by reference, may be used in combination with the embodiments of the present invention. While the above steps have been illustrated with a guidewire device configured according to FIG. 2A, it should be obvious that a similar process can be used with a guidewire device configured according to FIG. 2B, or with other variants of such guidewires.

It is noted that the guidewires of the present embodiments may comprise core wires of different types and configurations for providing improved torque and easy maneuvering through body vessels. In one embodiment, such a core wire is configured to have a cross-section with an aspect ratio of approximately one. In another embodiment, the core wire is configured to have a cross-section with an aspect ratio of less than one. In one embodiment, the core wire is configured to have a substantially flat cross-section. It is contemplated that the core wires may be stainless steel, Nitinol, Elgiloy, platinum, iridium, tantalum, titanium, cobalt, chromium, tungsten, combinations thereof, or other biologically compatible materials.

Optionally, it is noted that the guidewires of the present embodiments may comprise at least a layer of structural polymer over the core wire. Optionally, an outer surface of the first and/or the second guidewires are coated with hydrophilic coating for ease of navigation through tortuous passageways.

It is further contemplated that the guidewires may be configured to have a fixed length. In a double guidewire embodiment, such as that shown in FIG. 2A, the first guidewire and the second guidewire are each configured to be about 180 cm in length. Optionally, the first and second guidewires may be of different lengths. In a single guidewire embodiment, such as that shown in FIG. 2B, the guidewire device is configured to be about 300 cm from one head to the other head. Alternatively, the guidewires may be configured to be extendable.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for positioning a guidewire in an occluded body vessel, comprising:

advancing a guidewire in the occluded body vessel, wherein the guidewire consists of a monolithic core and a layer of structural polymer over the core wire, the core wire having a first head, a first tail, a second head, and a second tail, with the first tail and the second tail joined at a terminal end of the first tail and a terminal end of the second tail, the core wire further comprising a first length extending from the terminal end of the first tail to the first head and a second length extending from the terminal end of the second tail to the second head, wherein a flexibility of the core wire increases along the first length from the first tail to the first head and along the second length from the second tail to the second head and a cross-sectional area of the core wire decreases continuously along the entire said first length from the terminal end of the first tail to the first head and along the entire said second length from the terminal end of the second tail to the second head;

traversing an occlusion using the first head of the core wire; and advancing the guidewire through the occluded body vessel until the first head is retrieved out of the occluded body vessel.

2. The method of claim 1, further comprising penetrating a distal cap of the occlusion in a retrograde direction using the first head of the core wire.

3. The method of claim 1, further comprising penetrating a proximal cap of the occlusion in an antegrade direction using the first head of the core wire.

4. A device for recanalizing an occluded vessel, comprising:

a guidewire consisting of a monolithic core wire and a layer of structural polymer over the core wire, the core wire having a first head, a first tail, a second head, and a second tail, with the first tail and the second tail joined at a terminal end of the first tail and a terminal end of the second tail, the core wire further comprising a first length extending from the terminal end of the first tail to the first head and a second length extending from the terminal end of the second tail to the second head, wherein a flexibility of the core wire increases along the first length from the first tail to the first head and along the second length from the second tail to the second head and a cross-sectional area of the core wire decreases continuously along the entire said first length from the terminal end of the first tail to the first head and along the entire said second length from the terminal end of the second tail to the second head.

5. The device of claim 4, wherein the core wire comprises a substantially flat cross-section.

6. The device of claim 4, wherein an outer surface of the guidewire is coated with a hydrophilic coating.

* * * * *